(12) United States Patent
Tillery (10) Patent No.: US 7,597,245 B1
(45) Date of Patent: Oct. 6, 2009

(54) DENTAL IMPRESSION SHIPPING BOX

(76) Inventor: David Allen Tillery, 1901 Hand Ave., Bay Minette, AL (US) 36507

( * ) Notice: Subject to any disclaimer, the term of this patent is extended or adjusted under 35 U.S.C. 154(b) by 37 days.

(21) Appl. No.: 11/900,545

(22) Filed: Sep. 12, 2007

Related U.S. Application Data (60) Provisional application No. 60/845,449, filed on Sep. 18, 2006.

(51) Int. Cl.
  *B65D 81/02* (2006.01)
  *A61B 19/02* (2006.01)
(52) U.S. Cl. .................. 229/178; 206/63.5; 206/523; 206/583
(58) Field of Classification Search ............. 229/178; 206/63.5, 523, 521, 583, 587, 784, 485, 368
  See application file for complete search history.

(56) References Cited

U.S. PATENT DOCUMENTS

| | | | | | |
|---|---|---|---|---|---|
| 2,637,484 | A | * | 5/1953 | Buttery | 229/178 |
| 3,389,195 | A | * | 6/1968 | Gianakos et al. | 206/523 |
| 3,834,526 | A | * | 9/1974 | Zine, Jr. | 229/178 |
| 4,049,190 | A | | 9/1977 | O'Neill | |
| 4,173,286 | A | * | 11/1979 | Stanko | 206/523 |
| 4,211,322 | A | * | 7/1980 | Crescenzi et al. | 229/178 |
| 4,600,251 | A | | 7/1986 | Zimmerman | |
| 4,934,534 | A | * | 6/1990 | Wagner | 206/523 |
| 4,953,705 | A | * | 9/1990 | Evamy | 206/594 |
| 5,040,678 | A | * | 8/1991 | Lenmark et al. | 206/523 |
| 5,129,519 | A | * | 7/1992 | David et al. | 206/523 |
| 5,190,212 | A | | 3/1993 | Morris | |
| 5,356,006 | A | * | 10/1994 | Alpern et al. | 206/523 |
| 5,522,539 | A | * | 6/1996 | Bazany | 206/523 |
| 5,615,795 | A | * | 4/1997 | Tipps | 206/589 |
| 5,718,337 | A | * | 2/1998 | Carr et al. | 229/178 |
| 5,893,462 | A | | 4/1999 | Ridgeway | |
| 6,109,447 | A | | 8/2000 | Cabana | |
| 6,116,423 | A | * | 9/2000 | Troxtell et al. | 206/523 |
| 6,302,274 | B1 | | 10/2001 | Ridgeway | |
| 6,305,539 | B1 | * | 10/2001 | Sanders, Jr. | 206/523 |
| 6,431,363 | B1 | | 8/2002 | Hacker | |
| 6,622,860 | B2 | | 9/2003 | Horbal | |
| 6,675,970 | B1 | * | 1/2004 | Nemoto | 206/521 |
| 6,945,404 | B2 | | 9/2005 | Messinger | |
| 7,086,534 | B2 | | 8/2006 | Roesel | |
| 7,140,508 | B2 | | 11/2006 | Kuhn | |
| 7,172,109 | B2 | | 2/2007 | Kuenstler | |
| 2004/0079670 | A1 | * | 4/2004 | Sendijarevic et al. | 206/523 |

* cited by examiner

*Primary Examiner*—Gary E Elkins (57) ABSTRACT

The invention is a shipping box and an internal holding device designed to transport a dental impression without damage or distortion by suspending the impression by it's handle inside the box so that it does not touch the interior walls of the box. The box, constructed of fiberboard or plastic is divided into a receptacle, where the internal holding device secures the handle of the impression, and a suspension area, where the body of the impression is suspended in mid-air. The interior holding device is comprised of two blocks into which the handle of the impression will imprint, securing the impression and preventing it from moving about during transport.

4 Claims, 11 Drawing Sheets

DENTAL IMPRESSION SHIPPING BOX

CROSS-REFERENCE TO RELATED APPLICATIONS

This application claims the benefit of a Provisional Patent Application (Appl. No. 60/845,449) filed Sep. 18, 2006 by the present inventor.

FEDERALLY SPONSORED RESEARCH

N/A

SEQUENCE LISTING OR PROGRAM

N/A

BACKGROUND OF THE INVENTION

1. Field of Invention

My invention relates to a shipping box with an internal holding device, specifically to an improved way to ship a dental impression from the dental office to the dental laboratory without damaging or distorting the impression to such an extent that the appliance made from this impression will not fit the prepared tooth.

2. Discussion of Prior Art

My invention is a shipping box with an internal holding device designed to transport a dental impression (for crown or bridge work) without damage or distortion. My invention does this by suspending the impression by it's handle in mid-air inside the box using the internal holding device. Packing material is not needed.

Figure 1:
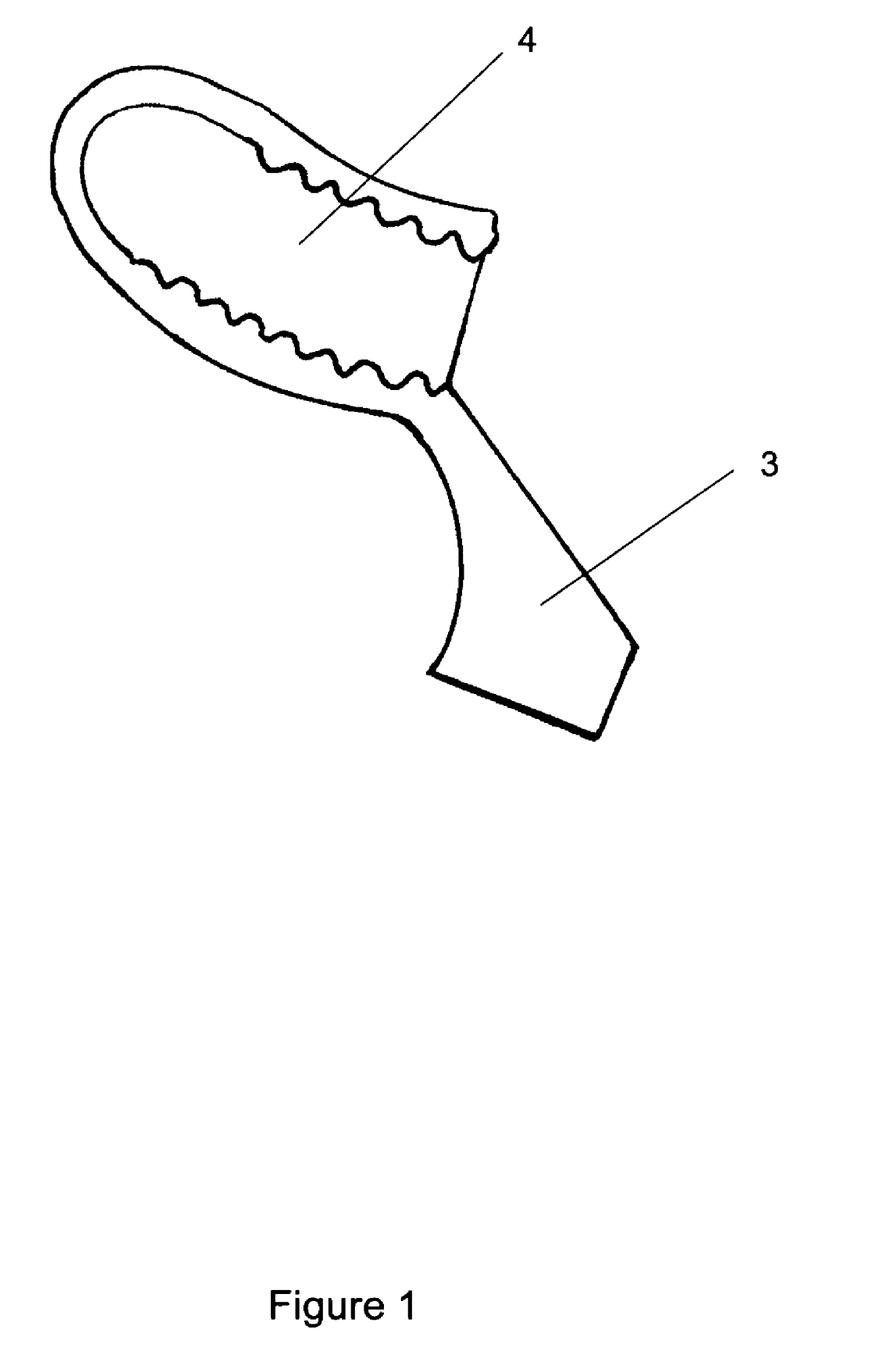
FIG. 1 is a triple tray used for the posterior part of the arch showing the handle and the body of the impression tray.

Most dental impressions for making crowns or bridges are taken with "triple trays". Triple trays are also referred to as bite trays, bite relation trays, 3-way trays, and dual arch trays. Triple trays are composed of a body (where the impression material is placed) and a handle (which sticks out of the mouth while the impression is being taken and is used to remove the tray from the mouth when the impression material is set). Triple trays are most often made of plastic and are flexible. Triple trays take an impression of the upper and lower arch as well as the bite all at the same time. Triple trays are made for the posterior part of the arch (FIG. 1), the anterior part of the arch, a complete quadrant, or a full arch.

Impressions for crowns and bridges are taken with a variety of impression materials—vinyl polysiloxane, polyether, silicone, and rubber base to name a few. When set, all these impression materials are flexible. Yet all have great memory when deformed and return with accuracy to their original shape. Impressions are almost always deformed to some degree simply by removing them from the mouth after they are set. Their recovery from this deformation is what makes them a great impression material. Without this characteristic crowns would rarely fit after being made from these impressions.

After removal from the mouth impressions are occasionally poured up in the office but most often are sent via the postal service or other carrier to the dental laboratory to be poured. At the present time impressions are boxed in the following manner using a traditional shipping box with an interior open space: place packing material in the bottom the box—place the impression on top of the packing material—finish filling (in some cases over filling) the box with packing material—close the lid and tape the box for shipping. If impressions are not packed properly, they can deform under pressure by compressing the packing material around the impression when the lid is closed. Allowed to remain in this deformed state for an extended period of time and under various environmental conditions, an impression may not regain its correct shape before it is poured. A crown made from such an impression would fit the die accurately but would not fit properly on the prepared tooth. My invention was designed to eliminate such a problem.

Figure 2:
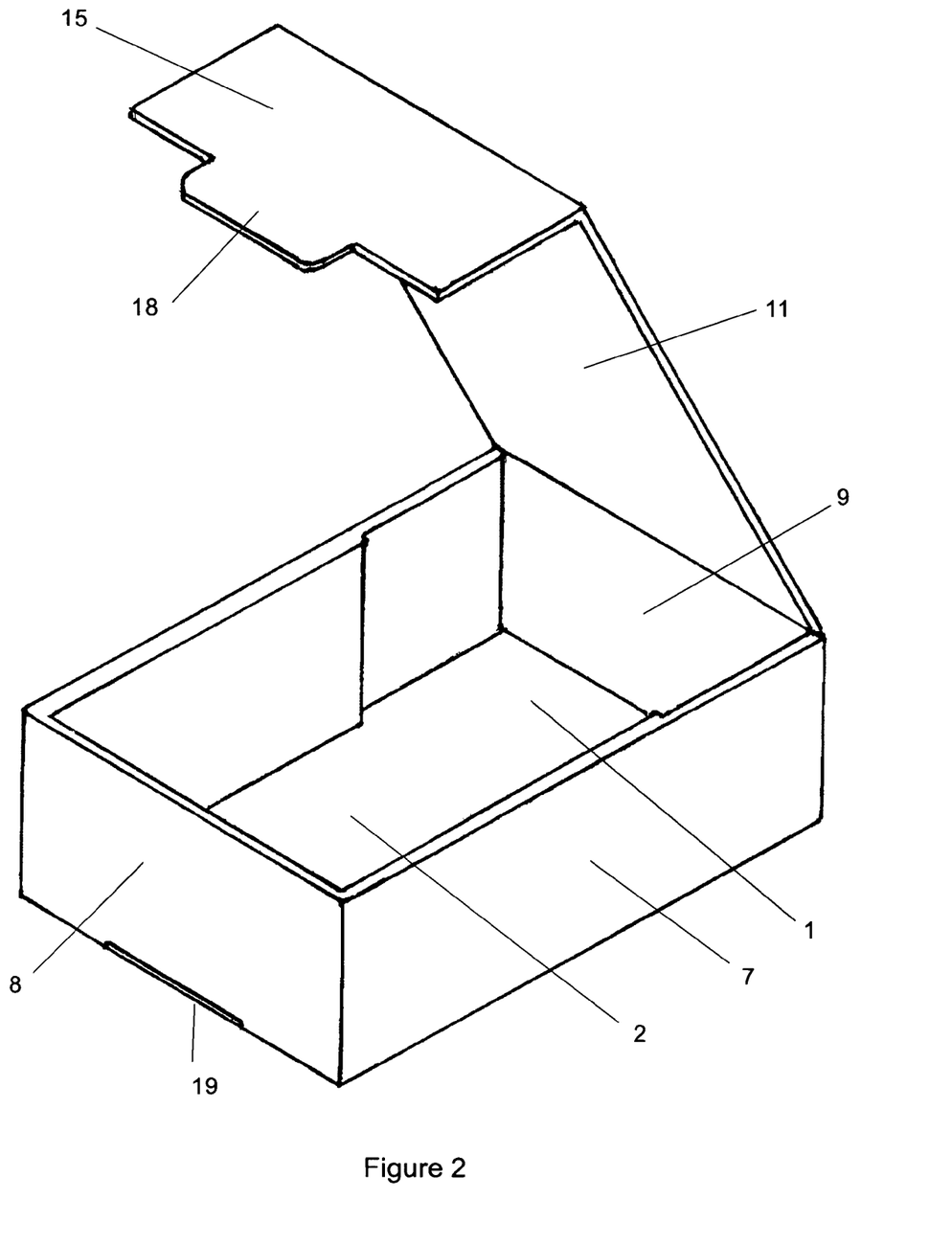
FIG. 2 is the shipping box of the invention showing the receptacle and the suspension area.

My invention consists of a shipping box with an internal holding device. The box is rectangular in length and width with two end walls, two side walls, a bottom and a lid. Unlike a standard shipping box with just an open space for the interior, the box of my invention has an interior space that is divided into a receptacle on one end for receiving an internal holding device and a suspension area on the other end where the body of the impression is suspended in mid-air (FIG. 2). These two areas are formed by placing stops on both side walls equidistant from one of the end walls. These stops run from the top to the bottom of the box and prevents the anterior displacement of the internal holding device when it is placed in the receptacle. The receptacle extends the full depth of the box and has the same length and width as the blocks of the internal holding device.

Figure 3:
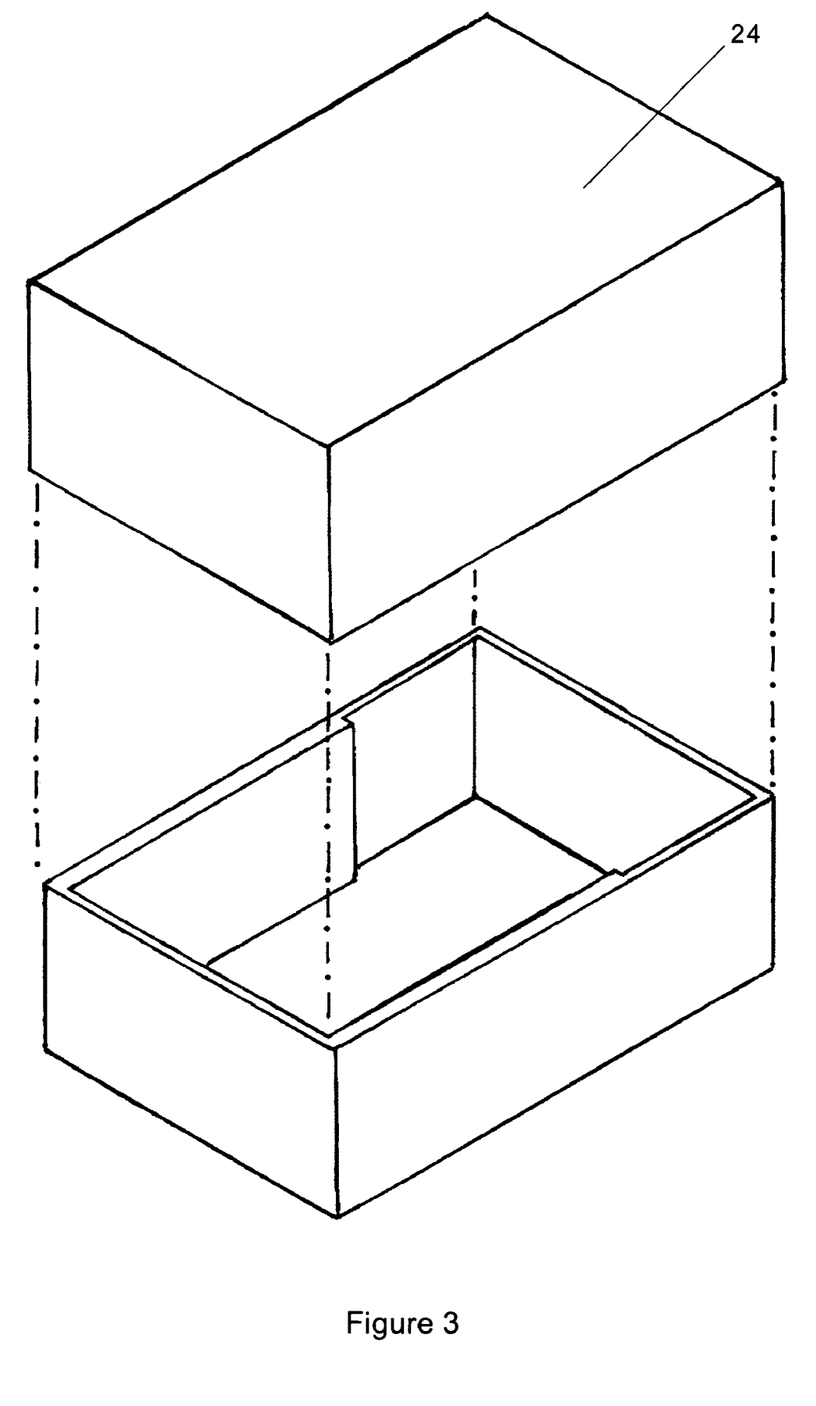
FIG. 3 is a shipping box with a full coverage removable lid
Figure 4:
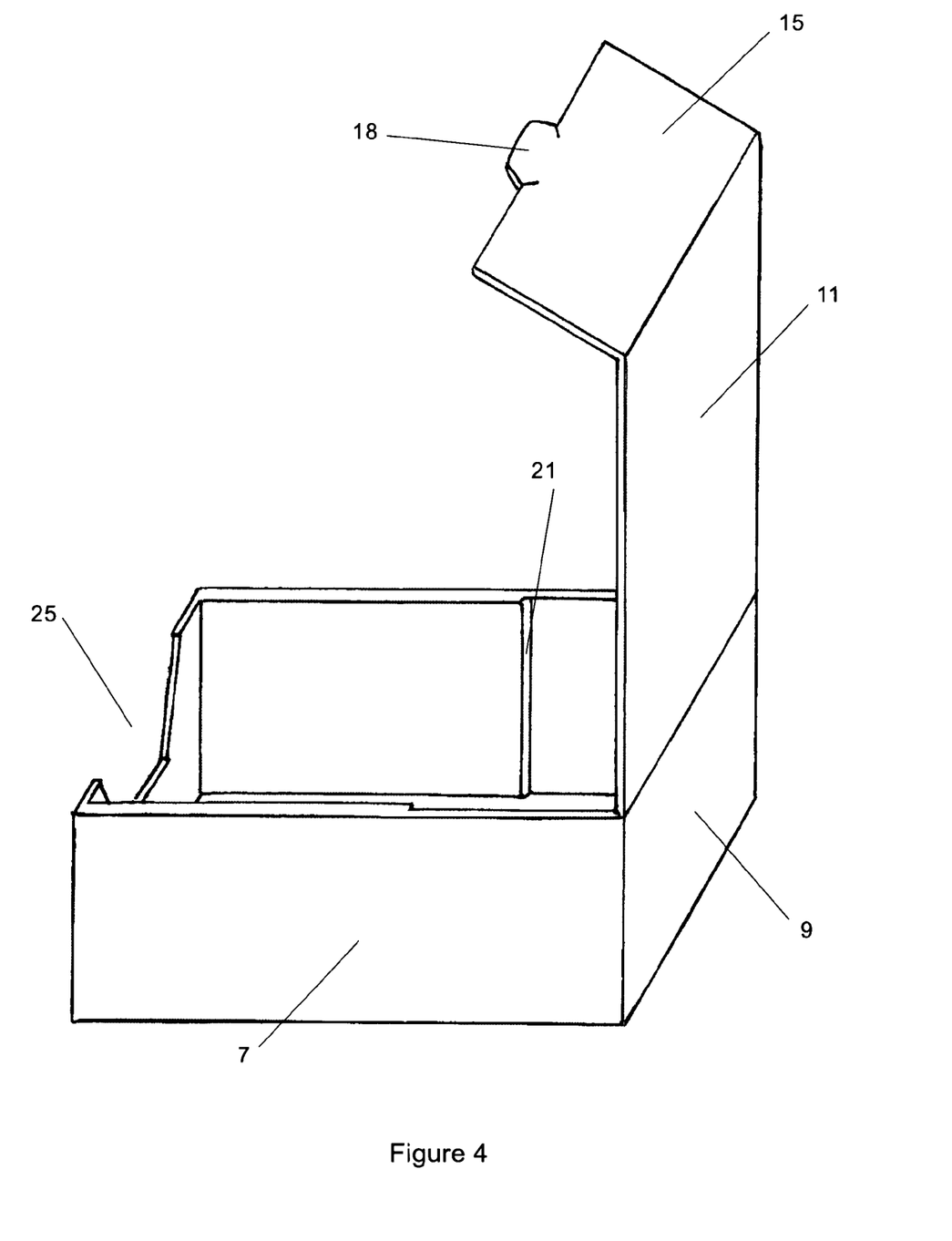
FIG. 4 is a shipping box with a hinged lid
Figure 5:
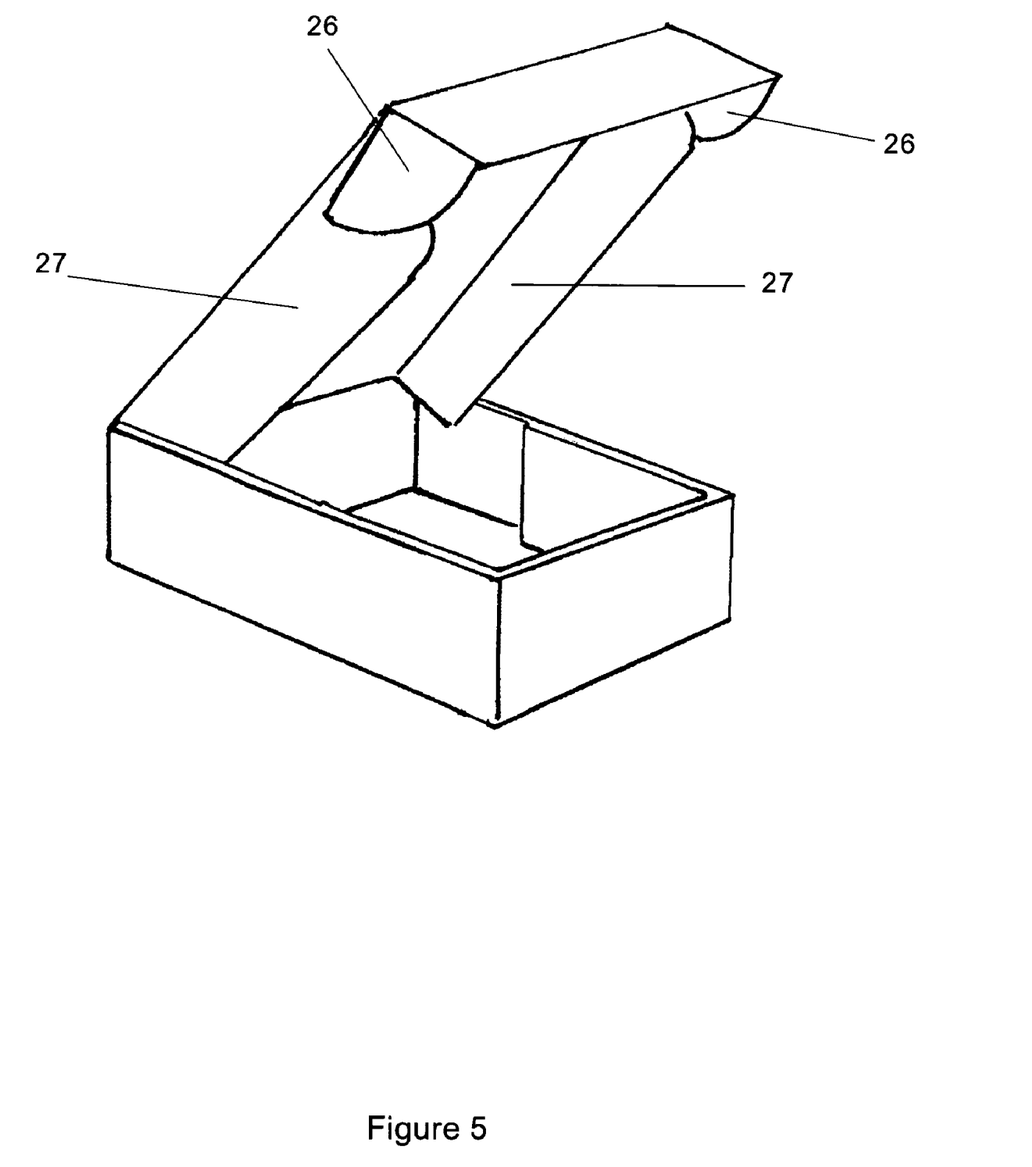
FIG. 5 is a shipping box with lock tabs off the sides of the lid as well as lock tabs off the front flap off the lid.

The lid of the shipping box can be removable (FIG. 3) or hinged (FIG. 4). If hinged, the lid has a front flap that folds down over the front wall. The front flap off the lid may have a tab off the front edge that inserts into a slot in the front wall to lock it closed or the front flap off the lid may have lock tabs off each side to do the same. The lid may also have lock tabs off each side (FIG. 5).

The box can be constructed of any material that is able to withstand the abuse parcels normally receive in transport. Paperboard and cellulosic or resinous material (plastic) are materials normally used for shipping boxes and either one can be used for this invention.

Figure 6:
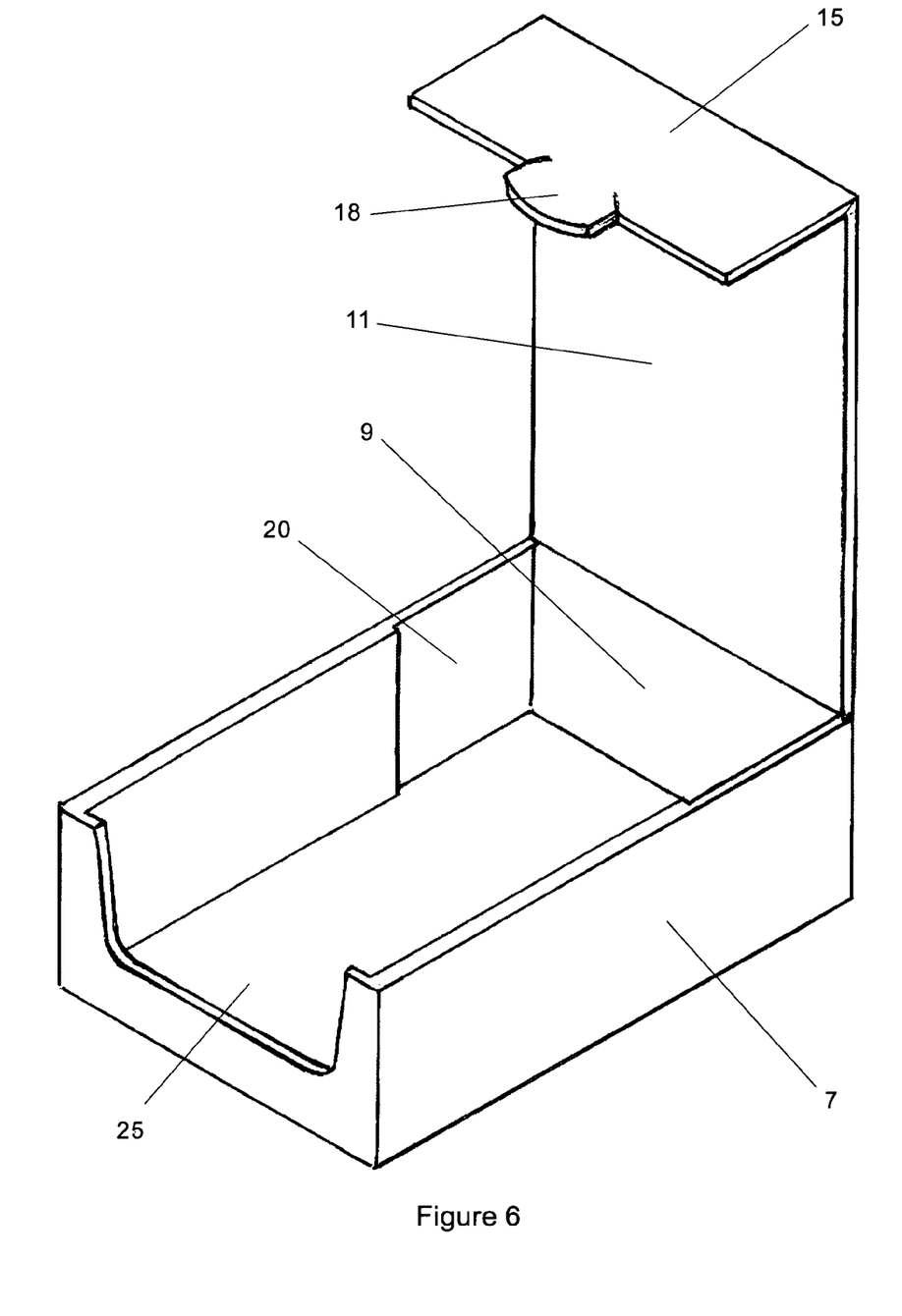
FIG. 6 is an example of a cutout used to facilitate the placement and removal of the internal holding device, this one being in the front wall of the box.

Cutouts may be added to the box to allow the hand to more easily place or remove the internal holding device and the impression from the receptacle in the box. Cutouts may be of any shape as long as they do not weaken the structural integrity of the box (FIG. 6).

The internal holding device will hold a dental impression securely by it handle while allowing the body of the impression to be held in mid-air. When the internal holding device is placed in the receptacle of the box, the body of the impression is held in mid-air inside the suspension area of the box and will not touch the interior walls of the box.

Figure 7:
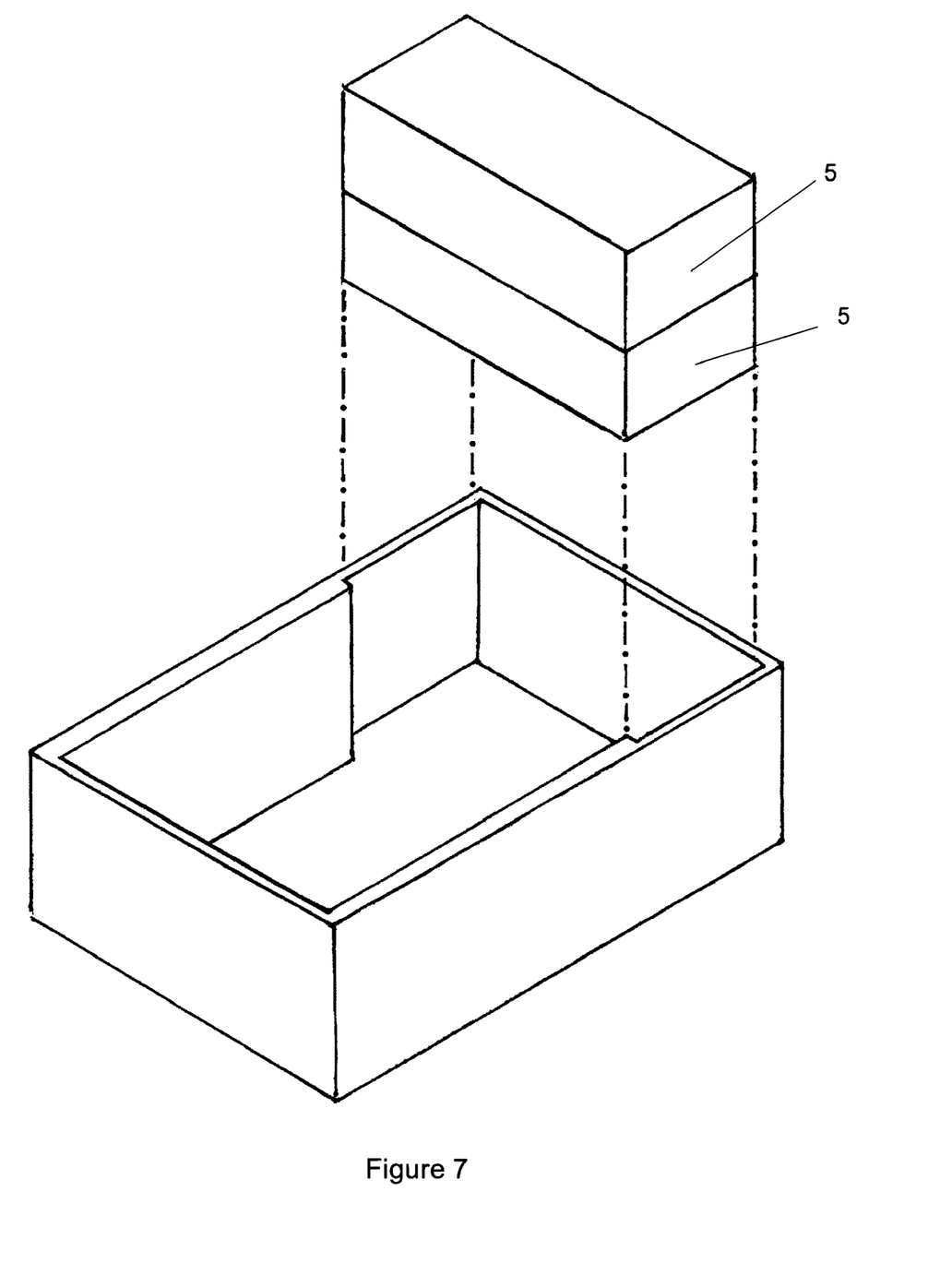
FIG. 7 shows how the internal holding device (the two blocks) is placed into the receptacle.
Figure 8:
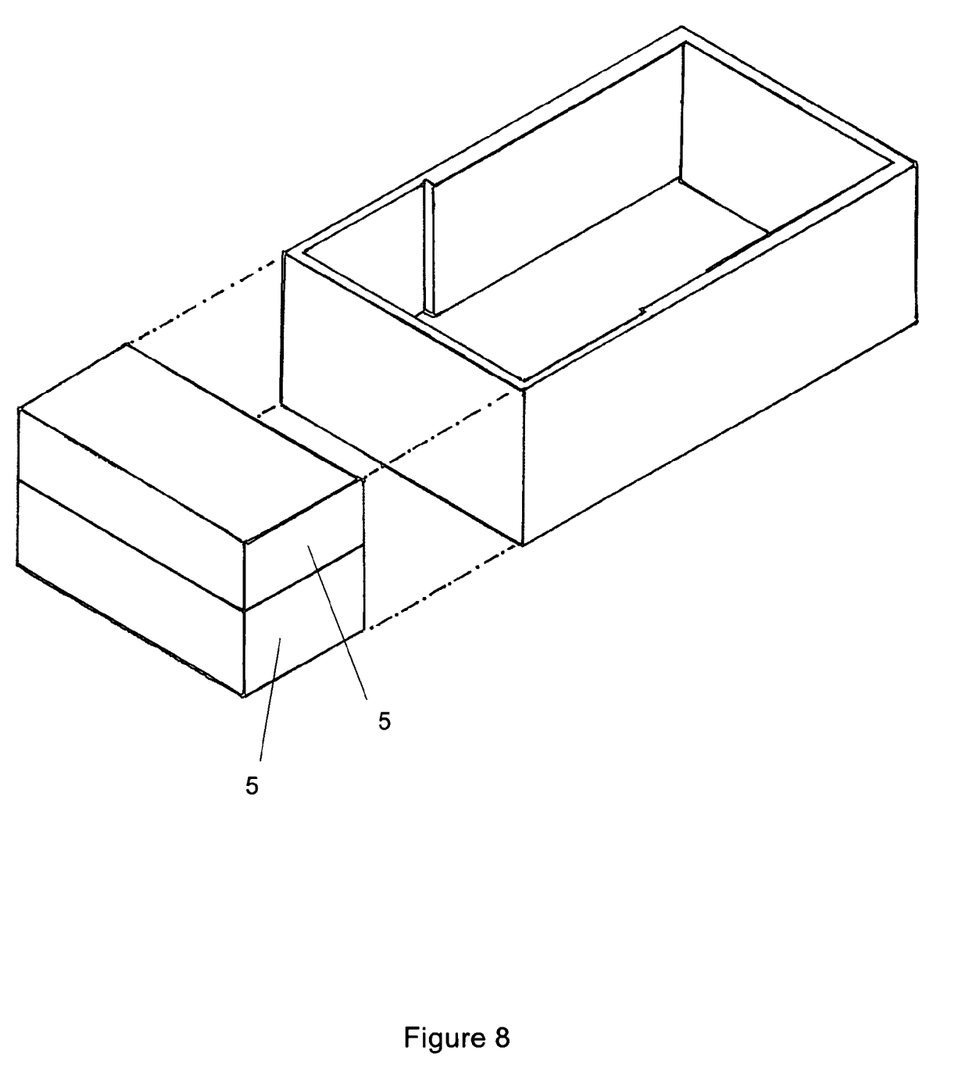
FIG. 8 shows how the internal holding device (the two blocks) has the same vertical height as the internal depth of the box.

The internal holding device of my invention is composed of two blocks. The two blocks should be of such length and width that they fit into the receptacle in the box (FIG. 7). When placed one on top of the other the two blocks should have the same thickness as the internal depth of the box (FIG. 8). When the two blocks are placed in the receptacle, the top of the blocks should be flush with the top of the box without the lid being closed. When the lid is closed, the two blocks are secure in the receptacle and cannot be dislodged.

Figure 9:
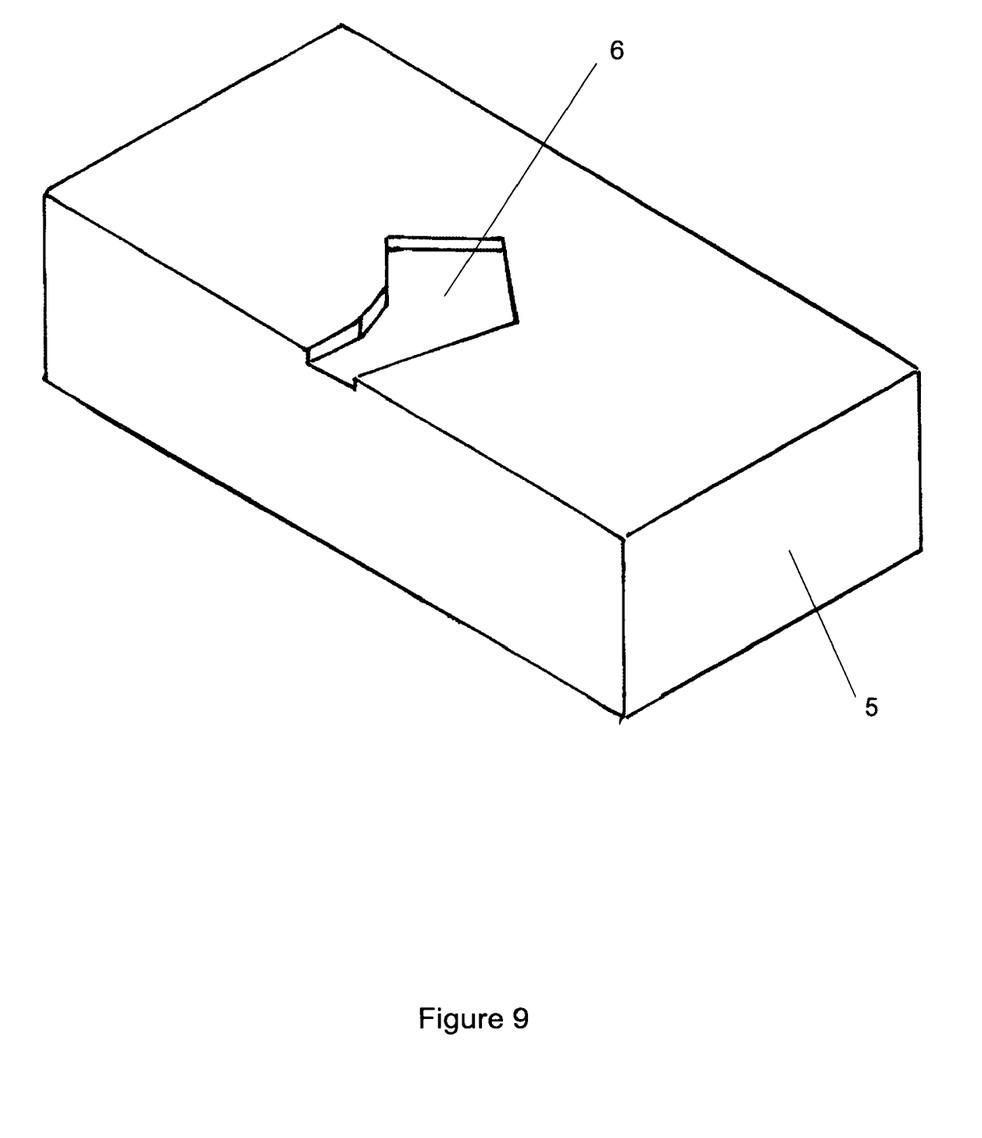
FIG. 9 shows how an imprint is made in one of the blocks when the handle of an impression is sandwiched between two blocks and compressed.

The two blocks of the internal holding device should be constructed of a material that can be imprinted. Polystyrene foam, styrofoam, and other similar materials imprint easily and work well as the blocks. The internal holding device depends on this imprinting of the blocks to secure the impression for transport. If the handle of an impression is sandwiched between the two blocks and the two blocks are compressed, an imprint of the handle of the impression is formed in the two blocks (FIG. 9). The two blocks are then fastened together with the handle of the impression embedded in the blocks. The two blocks can be secured together using tape, elastics, plastic ties, cord or any other device as long as the device does not hinder the placement or removal of the internal holding device from the receptacle in the box or does not prevent the closure of the lid. The two blocks with the handle of the impression embedded between them, is then slid down into the receptacle in the box. The body of the impression is positioned in the suspension area of the box, suspended so that it does not touch the sides, the bottom, or the end of the box. The lid is then closed, making sure that the lid does not touch the impression. The internal holding device with the impression is now secure in the box. The impression will not move, even if tossed about as it could be during transport The box is then taped and made ready for shipment.

All dentists have encountered this problem. The crown comes back from the lab. It fits the die perfectly but it will not fit the prepared tooth. This invention was designed to eliminate one possible cause—the deformation and distortion of the impression when boxed for transport.

OBJECTS AND ADVANTAGES

My invention will transport a dental impression from the dental office to the dental laboratory without damage of distortion, more safely than has ever been done before. The impression is held in the box by an interior holding device. Packing material is not required.

SUMMARY

My invention is a shipping box, similar to a standard shipping box but different in several ways. While a traditional shipping box only has an interior open space for shipping, my invention uses specifically located stops on the side walls to divide the interior of the box into two spaces, the receptacle and the suspension area. The receptacle is where the interior holding device is housed. The suspension area is where the body of the dental impression is held in mid-air so that the impression does not touch the interior walls of the box. Unlike the standard shipping box, the invention does not require any type of packing material.

DRAWINGS

Figures

LIST OF REFERENCE NUMERALS

1. Receptacle for the internal holding device
2. Suspension area for the body of the impression
3. Handle of the impression
4. Body of the impression
5. Block of the internal holding device
6. Imprint of the handle of an impression
7. Side wall of the box
8. Front wall of the box
9. Back wall of the box
10. Bottom of the box
11. Upper flap off the back wall—the lid of the box that is hinged
12. Upper flap off the side wall
13. Side flap off the back wall
14. Side flap off the front wall
15. Flap off the front of the lid
16. Tab off the upper flap off the side wall
17. Cutout in the bottom of the box
18. Tab off the front of the flap off the front of the lid
19. Slot in the front wall
20. Portion of the side wall—side wall of the receptacle
21. Anterior stop formed by a cut edge of the upper flap off the side wall
22. Section of the upper flap off the sidewall that have been cut away
23. Cut edge of the upper flap offside wall that will serve as an anterior stop for the receptacle when the box is assembled
24. Lid of a box that is removable
25. Cutout in the front wall of the box that allows the hand to more easily place and remove the internal holding device
26. Tab off the side of the flap off the front of the lid
27. Tab off the side of the lid

DETAILED DESCRIPTION OF THE PREFERRED EMBODIMENT(S)

Figure 10:
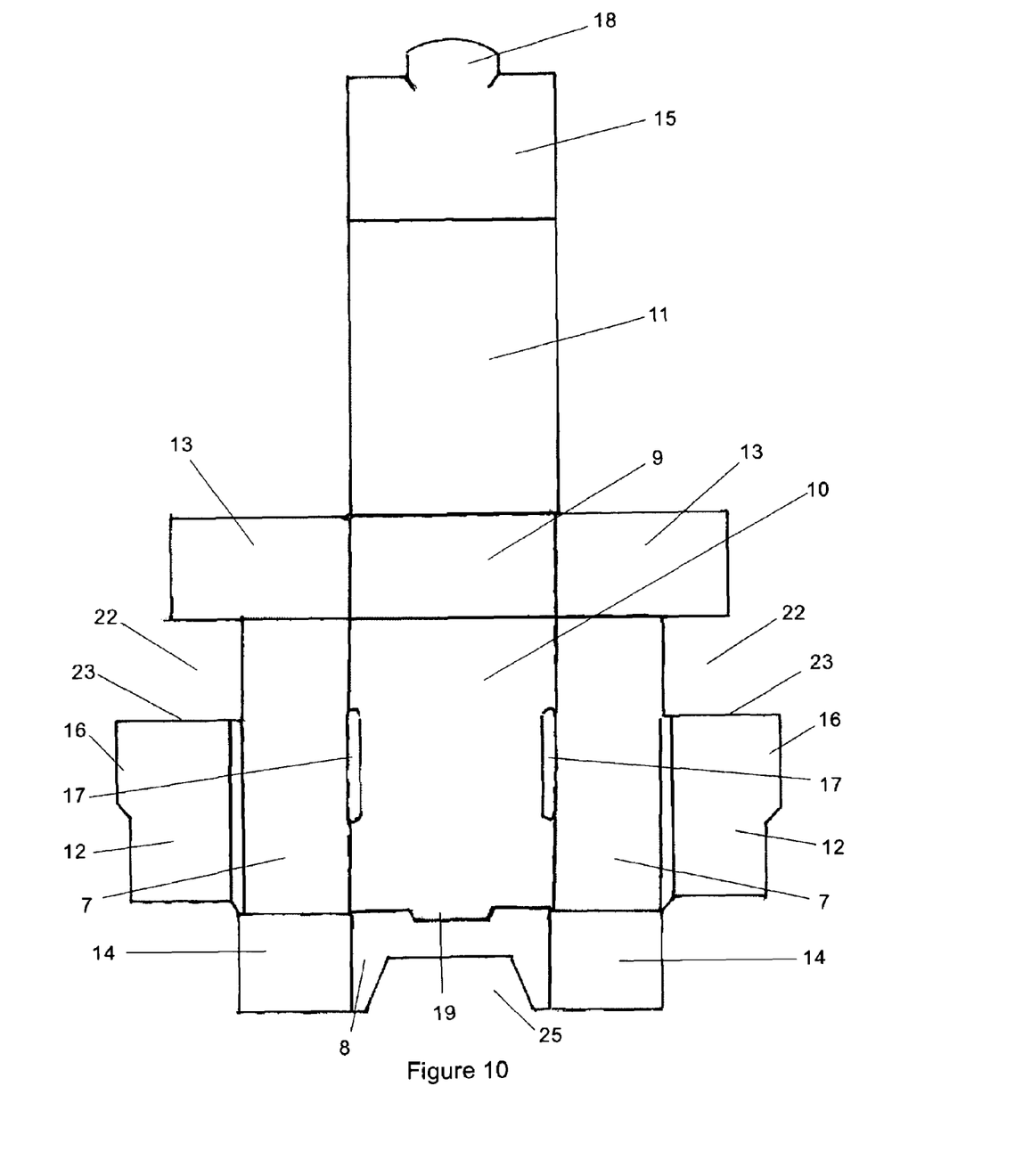
FIG. 10 shows the shipping box of the invention after it is cut from a single piece of fiberboard but before it is folded, this to demonstrate the difference between the box of the invention and a standard shipping box of similar design.
Figure 11:
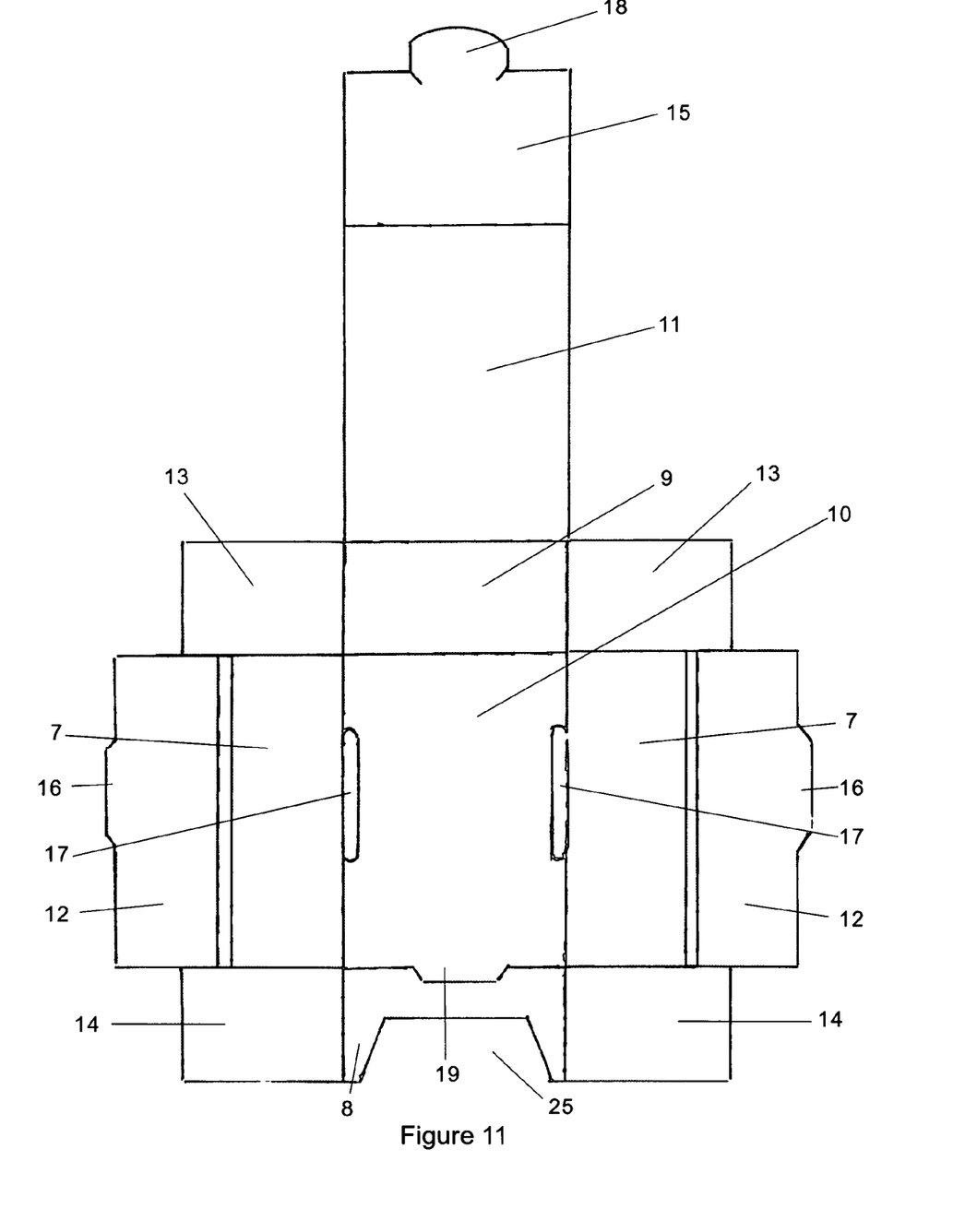
FIG. 11 shows a standard shipping box of similar design to the box of the invention after it is cut from a single piece of fiberboard but before it is folded, this one resulting in an interior open space.

My invention is a shipping box with an internal holding device. The box is cut from a unitary blank of corrugated paperboard and is folded along designated seams for assemblage. FIG. 10 shows the box after it is cut but before it is folded. FIG. 11 shows a standard shipping box of the same size and design after it is cut but before it is folded. FIG. 10 is compared to FIG. 11 to show how the box of my invention differs from a standard shipping box with an interior open space. A description of how my box differs is as follows:

1. Sections of the upper flaps off the side walls 22 are cut away. Cut edges of the upper flaps off the side walls 23 serve as the anterior stops 21 for the receptacle 1 when the box is assembled.

2. Cutouts in the bottom of the box 17 have been moved forward toward the front wall of the box 8.

3. The tabs off the upper flaps off the side walls 16 has been moved forward toward the front wall of the box 8 to correspond with the cutouts in the bottom of the box 17.

4. The side flaps off the front wall 14 have been shortened and the side flaps off the back wall 13 have been lengthened so that equal lengths of each will be covered by the upper flaps off the side walls 12 when the upper flaps off the side walls 12 are folded over the side flaps off the front wall 14 and side flaps off the back wall 13 and the tabs off the upper flaps off the side walls 16 are inserted into the cutouts in the bottom of the box 17.

The box is folded in the following manner to complete assemblage and to form a receptacle for the internal holding device.

1. Fold the side flaps off the front wall 14 and the side flaps off the back wall 13 up at 90 degrees.

2. Fold the front wall of the box 8 and the back wall of the box 9 up at 90 degrees causing the side flaps off the front wall 14 and the side flaps off the back wall 13 to approximate each other end to end.

3. Fold the upper flaps off the side walls 12 over the approximated side flaps off the front wall 14 and side flaps off the back wall 13 and insert the tabs off the upper flaps off the side walls 16 into the cutouts in the bottom of the box 17.

4. The upper flap off the back wall (the lid) 11 can then be closed. The flap off the front of the lid 15 is closed over the front wall 8 and the tab off the flap off the front of the lid 18 is inserted into the slot in the front wall 19, effectively completing the assemblage of the box.

Rectangular sections of the upper flaps off the side walls 22 have been cut away. As a result, when the upper flaps off the side walls 12 are folded over and the tabs off the upper flaps off the side walls 16 are inserted into the cutouts in the bottom of the box 17, anterior stops 21 are created and the receptacle 1 for the interior holding device is complete. The walls of the receptacle 1 are the back wall of the box 9, a portion of the two side walls 20, and the anterior stops formed by the cut edge of the upper flaps off the side walls 21. The remainder of the interior of the box from the anterior stops 21 to the front wall of the box 8 constitutes the suspension area 2 and is where the body of the impression 4 is held in mid-air.

The interior holding device consists of two blocks 5 of virgin expanded polystyrene (1.0 lb. density). Each block 5 has the same length and width as the receptacle 1. When both blocks 5 are stacked in the receptacle 1, one on top of the other, the top of the blocks 5 is flush with the top of the box without the lid 11.

When the handle of the impression 3 is placed between the two blocks 5 and the two blocks 5 are compressed, an imprint of the handle 6 is made in the blocks. With the handle of the impression 3 embedded between the two blocks 5, the two blocks 5 are secured by encircling the two blocks 5 with transparent adhesive tape. Because of the imprinting, the vertical dimension of the two blocks 5 is not changed. With the handle of the impression 3 embedded in the two blocks 5, the internal holding device is placed in the receptacle 1. The body of the impression 4 is suspended in mid-air in the suspension area 2 and will not touch the interior walls of the box. The lid 11 is closed and the boxed is taped.

Alternative Embodiments

There are many ways to construct a mailer box that is different from the way described in the preferred embodiment. Regardless of the way that it is constructed or the material used, this invention is meant to include all shipping boxes that are divided into a receptacle for an internal holding device and a suspension area for the suspension of the body of the impression by an anterior stop intended to keep the internal holding device from being displaced anteriorly.

There are other ways to construct an internal holding device other than the one described in the preferred embodiment that will secure the handle of an impression and fit into the receptacle. None are more effective than the two blocks and all are more expensive. These include devices with screws, clips, elastics as well as other methods for securing the handle of the impression. The scope of this invention includes all such devices

CONCLUSION, RAMIFICATIONS, AND SCOPE OF THE INVENTION

This invention provides a safe, reliable, lightweight, and economical way to ship a dental impression from the dental office to the dental laboratory. The invention holds the body of a dental impression inside the box in mid-air rather than surrounding it with packing material.

There are many variations to the way a standard shipping box can be cut and assembled that will result in an interior open space for shipping. The difference between the invention and a standard shipping box is not how it folds for assemblage or how the various tabs lock the box together but the anterior stop that divides the interior space into two areas—a receptacle and a suspension area—and prevents the anterior displacement of the internal holding device inside the box. There are many ways that can be devised to build a holding device that will secure a dental impression by it's handle and fit into the receptacle in the box—devices with screws, devices with clips, and so on. These devices are far more expensive yet no more reliable than the two imprintable blocks of my invention. The scope of my invention includes all such alternative devices that will hold a dental impression securely by it's handle, suspend the body of the impression in the suspension area, and fit securely into the receptacle created in the shipping box.

The invention claimed is:

1. A box comprising:
   a front wall, a back wall, a bottom wall and two side walls extending between said front and back walls,
   a lid foldably connected to said back wall
   said side walls each including an outer wall and an inner wall folded inwardly from a top of said outer wall, a stop formed by a rear edge of each inner side wall, said edges, bottom wall, outer side walls and back wall together forming a rear compartment in said box, said inner side walls, bottom wall and front wall together forming a front compartment in said box,
   two foam blocks within said rear compartment, said foam blocks together having substantially the same dimensions as said rear compartment and engaging the stops to prevent shifting during transport,
   whereby said foam blocks being dimensioned and positioned within the rear compartment such that the foam blocks are adapted to receive a handle of a triple tray crown or bridge dental impression with a body of the triple tray dental impression protruding from the foam blocks into the front compartment.

2. A box as set forth in claim 1, wherein
   said foam blocks are rectangular and stacked on top of each other within the rear compartment.

3. A box as set forth in claim 1, wherein
   said box further including a handle secured within said foam blocks and a triple tray crown or bridge dental impression, said triple tray dental impression suspended from said handle into the front compartment with said dental impression not touching the side walls, the front wall, the bottom wall or said lid, when said lid is closed.

4. A method of using a box comprising:

providing a box with two foam blocks as set forth in claim 1, placing a handle of a triple tray crown or bridge dental impression between said two foam blocks with said dental impression extending from said foam blocks, fixedly securing said blocks together with said handle secured there between, placing said secured blocks within the rear compartment of said box with said impression extending into the front compartment, and closing the lid of said box.

* * * * *